(12) United States Patent
Williams et al.

(10) Patent No.: US 6,863,648 B2
(45) Date of Patent: Mar. 8, 2005

(54) BALLOON PUMP SYSTEM HAVING A PRESSURE RESERVOIR MUFFLER

(75) Inventors: Jonathan Williams, Montville, NJ (US); Robert Hoff, Cedar Grove, NJ (US); Yefim Kaushansky, Fairlawn, NJ (US)

(73) Assignee: Datascope Investment Corp., Montvale, NJ (US)

( * ) Notice: Subject to any disclaimer, the term of this patent is extended or adjusted under 35 U.S.C. 154(b) by 330 days.

(21) Appl. No.: 09/817,317

(22) Filed: Mar. 26, 2001

(65) Prior Publication Data

US 2002/0137981 A1 Sep. 26, 2002

(51) Int. Cl.$^7$ ............................................. A61B 1/362
(52) U.S. Cl. ........................................ 600/18; 623/3.16
(58) Field of Search ....................... 600/16–18; 623/3.1, 623/3.11, 3.16, 3.21, 3.28, 3.17, 3.18

(56) References Cited

U.S. PATENT DOCUMENTS

| | | | |
|---|---|---|---|
| 4,905,789 A | | 3/1990 | Francis |
| 4,923,451 A | | 5/1990 | McCormick |
| 5,345,928 A | | 9/1994 | Lindkvist |
| 5,380,267 A | * | 1/1995 | Boutelle et al. ............. 600/18 |
| 5,829,492 A | | 11/1998 | Gavronsky et al. |
| 6,148,631 A | | 11/2000 | Watanabe et al. |

* cited by examiner

*Primary Examiner*—Angela D. Sykes
*Assistant Examiner*—Roderick Bradford
(74) *Attorney, Agent, or Firm*—J. Gary Mohr

(57) ABSTRACT

A vacuum reservoir, for use with an intra-aortic balloon pump or other system, containing a muffling means having a honeycomb-like cell structure or other flow straightening structure.

14 Claims, 5 Drawing Sheets

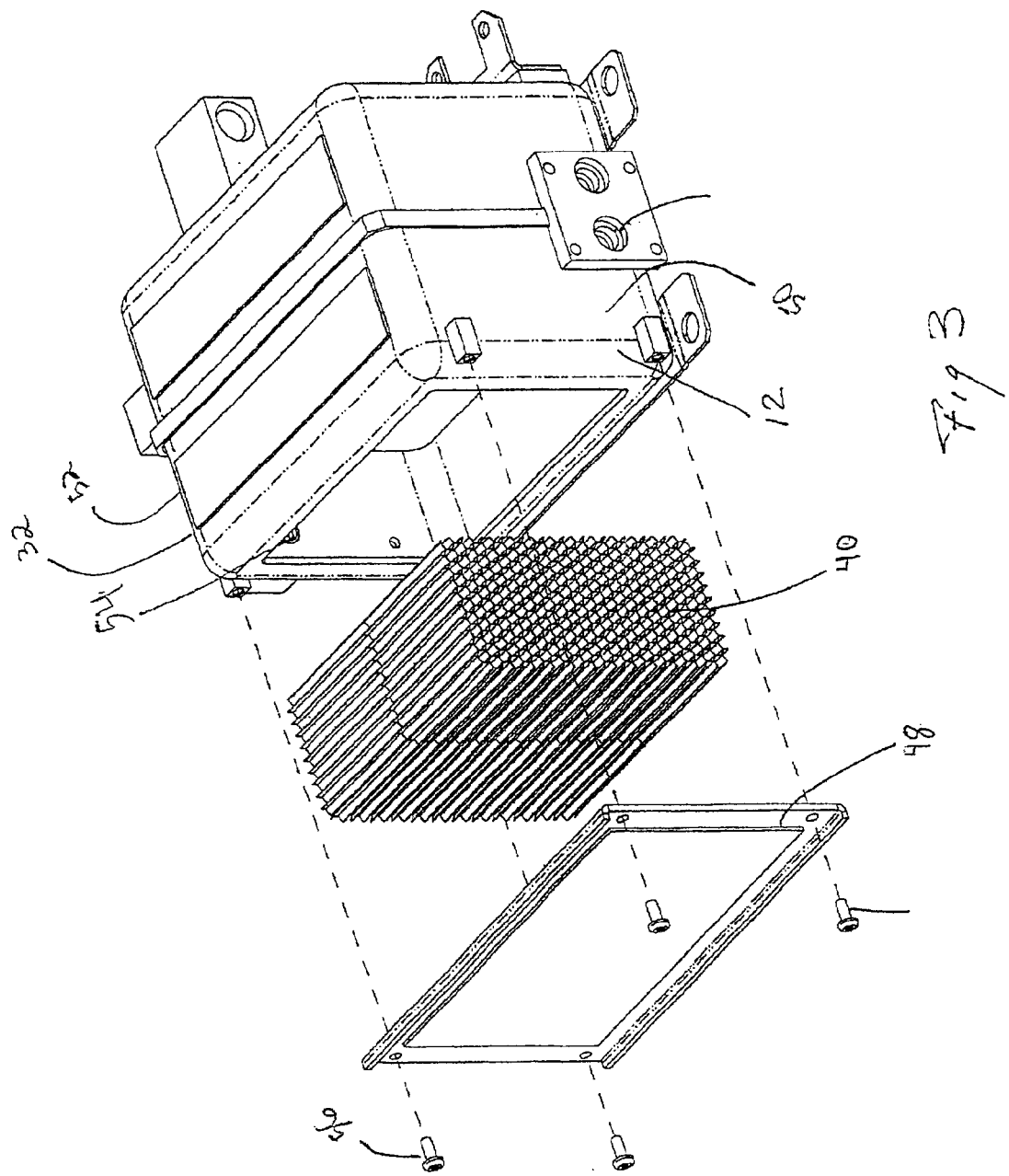

BALLOON PUMP SYSTEM HAVING A PRESSURE RESERVOIR MUFFLER

BACKGROUND OF THE INVENTION

1. Field of the Invention

The invention relates to an enhanced quieter intra-aortic balloon pump system. More particularly, the invention relates to a muffling device for a vacuum pressure reservoir commonly used in intra-aortic balloon pump systems.

2. Description of the Prior Art

Intra-aortic balloon pump therapy is frequently prescribed for patients who have suffered a heart attack or some other form of heart failure. In such therapy, a thin balloon is inserted through an artery into the patient's aorta. The balloon is connected through a series of thin tubes to a complex apparatus which causes the balloon to inflate and deflate repeatedly in time with the patient's heart beat, thereby assuming some of the load of the heart during the patient's recovery period.

The inflation/deflation apparatus supplies positive pressure for expanding the balloon during an inflation cycle and negative pressure for contracting the balloon during a deflation cycle. In a conventional prior art apparatus, shown schematically in FIG. 1, an intra-aortic balloon 10 is inserted into a patient's aorta and is connected through small profile catheter 12 and a larger profile extender 14 to an isolator 18 divided by a pliant membrane 20 into an input or primary side 22 and a secondary side 24. The entire volume between membrane 20 and balloon 10 is typically filled with a gas, such as helium, supplied by a gas source 26. A positive pressure reservoir 28 is connected through a solenoid valve 30 to the input or primary side 22 of isolator 18. Similarly, a negative pressure reservoir 32 is connected through a solenoid valve 34 to the input or primary side 22 of isolator 18. The primary side 22 of isolator 18 is also connected through a solenoid valve 36 to a vent or exhaust port 38. A compressor 11 is connected to both positive pressure reservoir 28 and negative pressure reservoir 32. By pumping the gas into pressure reservoir 28 and out of negative pressure reservoir 32 at a predetermined rate, compressor 11 assures that positive pressure reservoir 28 is available, at the necessary capacity, for each inflate cycle of balloon 10 and that negative pressure reservoir 32 is available, at the necessary capacity, for each deflate cycle of balloon 10.

During an inflation cycle, solenoid valve 30 is opened to permit positive pressure from positive pressure reservoir 28 to enter primary side 22 of isolator 18. This positive pressure causes membrane 20 to move toward secondary side 24, thereby forcing the helium in the secondary side to travel toward and inflate balloon 10. For deflation, solenoid valve 30 is closed and solenoid valve 36 is opened briefly to vent the gas from primary side 22, after which valve 36 is closed. Solenoid valve 34 is then opened, whereupon negative pressure reservoir 32 creates a negative pressure on the primary side 22 of isolator 18. This negative pressure pulls membrane 20 toward primary side 22, whereby the helium is drawn out from the balloon. Compressor 11 continuously replenishes the positive pressure in positive pressure reservoir 28 and the vacuum in negative pressure reservoir 32.

It is desirable in intra-aortic balloon pump therapy to inflate and deflate the balloon as rapidly as possible. Rapid cycling permits the therapy to be performed more effectively, and enables smaller diameter catheters to be used, thereby reducing the possibility of limb ischemia. Although the prior art system described above permits rapid inflation and deflation cycles, the configuration of this system, specifically the burst of air flow into vacuum reservoir 32 upon the activation of the solenoid valve 34, creates an undesirable "rushing" sound. The vacuum reservoir of the present invention includes a honeycomb structure positioned perpendicular to the jet flow, which spreads the gas stream evenly across vacuum reservoir 32 and reduces the above mentioned "rushing" sound.

Mufflers typically are designed in one of three ways: with staggered baffles, with sound defeating angles or with fiberglass packing. Unlike traditional mufflers, the above mentioned honeycomb structure, does not create significant flow restrictions. Various devices for directing and muffling airflow are known, but the inventors are not aware of any prior use of a honeycomb or similar structure as a muffler; more specifically, the inventors are not aware of any prior incorporation of a honeycomb or other flow straightening structure into a vacuum reservoir for muffling purposes.

While present day intra-aortic balloon pump systems, vacuum reservoirs, and mufflers in general may be suitable for the particular purposes employed, or for general use, they are not as suitable for the purposes of the present invention as disclosed hereafter.

SUMMARY OF THE INVENTION

Accordingly, it is an object of the invention to produce a quieter intra-aortic balloon pump system.

More generally it is an object of the invention to produce a device which muffles the sound produced by the release of a jet of gas or fluid.

The invention is a vacuum reservoir, for use with an intra-aortic balloon pump or other system, containing a muffling means having a honeycomb-like cell structure or other flow straightening structure.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 3 is a perspective view of the vacuum and pressure reservoir of FIG. 2 with a side wall removed and the muffling means pulled out.

DETAILED DESCRIPTION OF THE PREFERRED EMBODIMENTS

Figure 1:
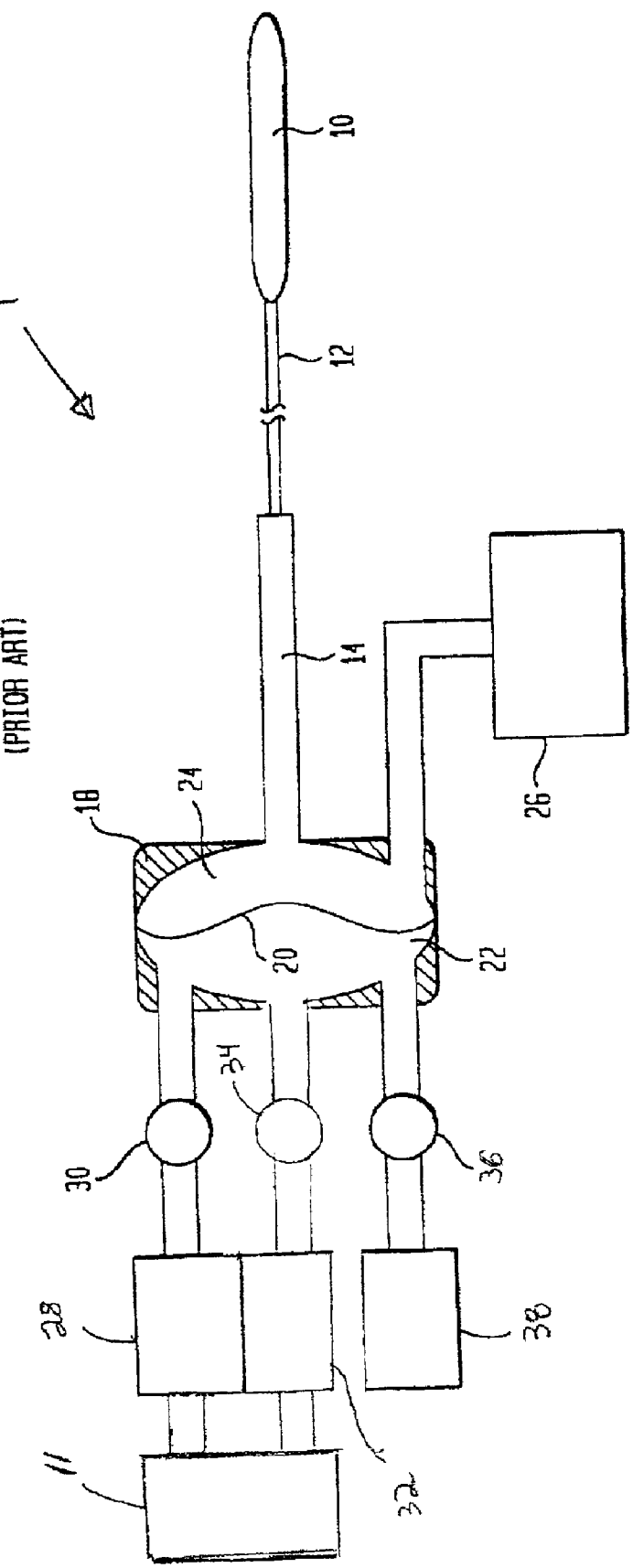
FIG. 1 is block diagram of a prior art intra-aortic balloon pump system.

FIG. 1 illustrates a prior art intra-aortic balloon system 1 comprising an intra-aortic balloon catheter 12, an extender 14 connecting said intra-aortic balloon catheter 12 to an isolator 18, a gas source 26, a compressor 11, a vent 38, and a positive pressure reservoir 28 and negative pressure reservoir 32 connected in parallel between compressor 11 and isolator 18. Intra-aortic balloon catheter terminates in a balloon 10. Isolator 18 comprises an enclosed volume divided by a pliant membrane 20 into a primary side 22 and a secondary side 24. The entire volume between membrane 20 and balloon 10 is typically filled with a gas, such as helium, supplied by gas source 26. Positive pressure reservoir 28 is connected through a solenoid valve 30 to the input or primary side 22 of isolator 18. Similarly, negative pressure reservoir 32 is connected through a solenoid valve 34 to the input or primary side 22 of isolator 18. Both positive pressure reservoir 28 and negative pressure reservoir 32 are essentially empty volumes. Primary side 22 of isolator 18 is also connected through a solenoid valve 36 to a vent or exhaust port 38. Compressor 11 is connected to both positive pressure reservoir 28 and negative pressure reservoir 32. By pumping the gas into pressure reservoir 28 and out of negative pressure reservoir 32 at a predetermined rate, compressor 11 assures that positive pressure reservoir 28 is available, at the necessary capacity, for each inflate cycle of balloon 10 and that negative pressure reservoir 32 is available, at the necessary capacity, for each deflate cycle of balloon 10. A processor or other logic component, not shown, is used to control solenoid valves 30, 34, and 36. Note that solenoid valves 30, 34, and 36 may be replaced with other types of valves or any other known control means for controlling flow known in the art.

During an inflation cycle, solenoid valve 30 is opened to permit positive pressure from positive pressure reservoir 28 to enter primary side 22 of isolator 18. This positive pressure causes membrane 20 to move toward secondary side 24, thereby forcing the helium in the secondary side to travel toward and inflate balloon 10. For deflation, solenoid valve 30 is closed and solenoid valve 36 is opened briefly to vent the gas from primary side 22, after which valve 36 is closed. Solenoid valve 34 is then opened, whereupon negative pressure reservoir 32 creates a negative pressure on the primary side 22 of isolator 18. This negative pressure pulls membrane 20 toward primary side 22, whereby the helium is drawn out from balloon 10. Compressor 11 continuously replenishes the positive pressure in positive pressure reservoir 28 and the vacuum in negative pressure reservoir 32.

Figure 2:
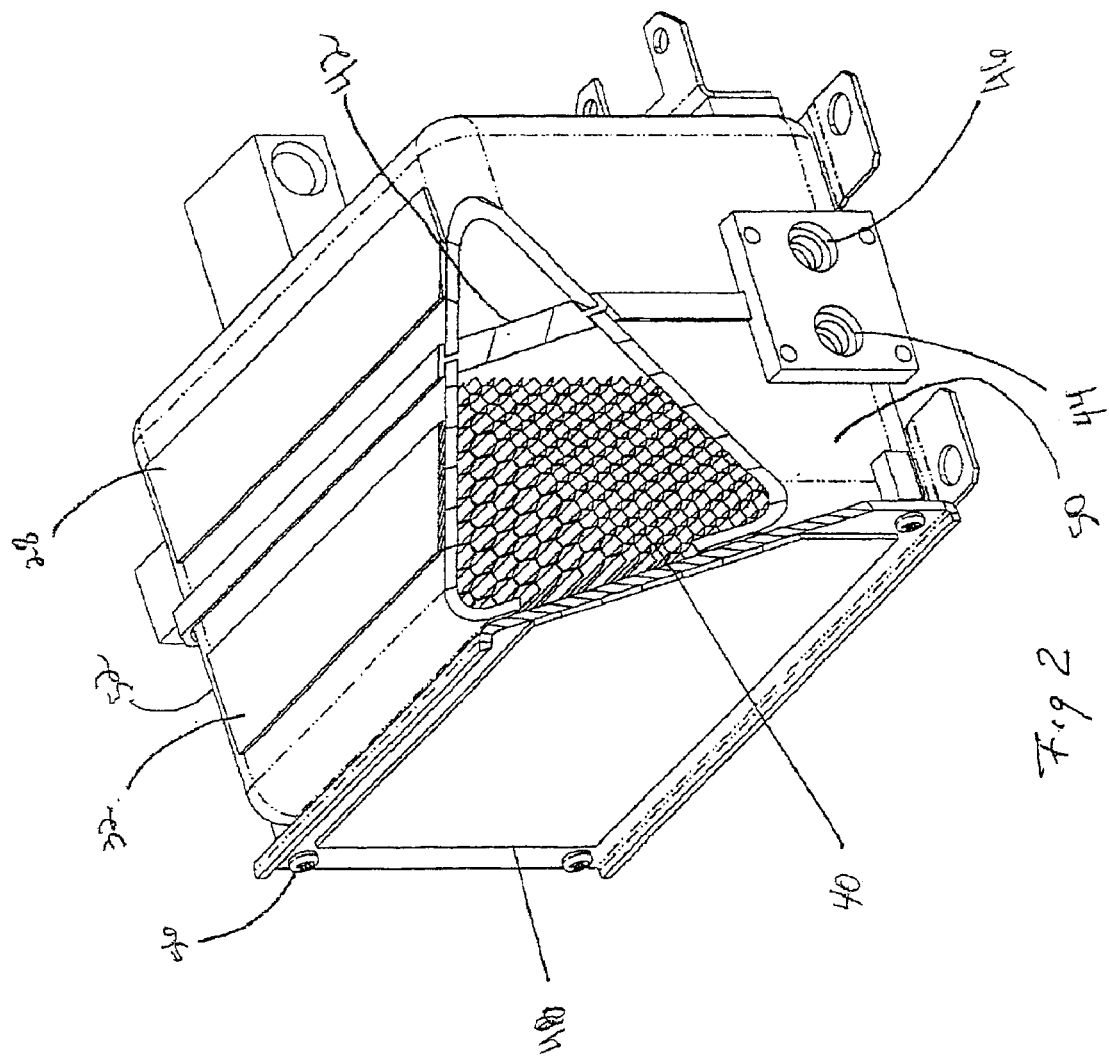
FIG. 2 is perspective view of vacuum and pressure reservoir unit incorporating the honeycomb structure of the present invention in the vacuum reservoir.

It is desirable in intra-aortic balloon pump therapy to inflate and deflate the balloon as rapidly as possible. Rapid cycling permits the therapy to be performed more effectively, and enables smaller diameter catheters to be used, thereby reducing the possibility of limb ischemia. Although the prior art system described above permits rapid inflation and deflation cycles, the configuration of this system, specifically the burst of air flow into vacuum reservoir 32 upon the activation of the solenoid valve 34, creates an undesirable "rushing" sound. FIG. 2 illustrates an improved negative pressure reservoir 32 and positive pressure reservoir 28 attached side-to-side. For illustration purposes, a corner of the negative pressure reservoir 32 is cut off so as to expose a muffling means 40, positioned perpendicular to the jet flow, contained within the negative pressure reservoir 32. Muffling means 40 has a honeycomb structure. The purpose of honeycomb structure is to reduce noise upon the entrance of the gas into negative pressure reservoir 32 through port 44. Negative pressure reservoir 32 and positive pressure reservoir 28 are separated by a shared wall 42, a corner of which is also cut off for illustration purposes. Negative pressure reservoir 32 has a forward wall 50 and a rearward wall 52. Muffling means 40 does not fill the entire negative pressure reservoir 32, gaps exist between forward wall 50 and muffling means 40 and also between muffling means 40 and rearward wall 52. Port 46 provides access to positive pressure reservoir 28. Compressor 11 (FIG. 1) is connected to a port 54(FIG 3) on rearward wall 52 and to a port (not shown) on a rearward end of positive pressure reservoir 28. Note that negative pressure reservoir 32 and positive pressure reservoir 28 may also be made as independent units without a shared wall. Note further that each reservoir may have a pneumatic regulator (not shown). If the pressure in the reservoir exceeds the regulator's set point, then the regulator vents the reservoir to atmosphere. Note that use any type of reservoir known in the art, including variable volume reservoirs, capable of accommodating muffling means 40 is anticipated.

FIG. 3 illustrates muffling means 40 removed from negative pressure reservoir 32 and removable wall 48 detached from negative pressure reservoir 32. Screws 56, or other known attachment means, are used to connect wall 48 to negative pressure reservoir 32. Removal of muffling means 40 exposes port 54.

Figure 4A:
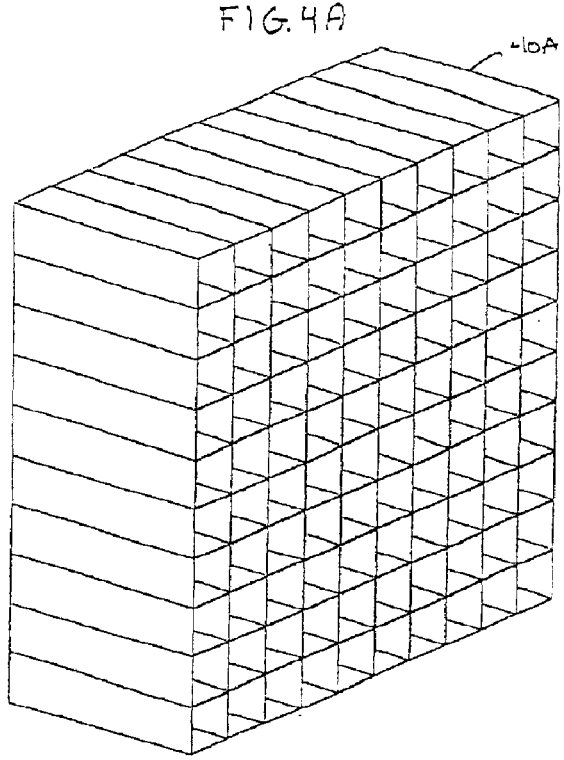
FIG. 4A is a perspective view of an alternate embodiment of the muffling means having repeating square cells.
Figure 4B:
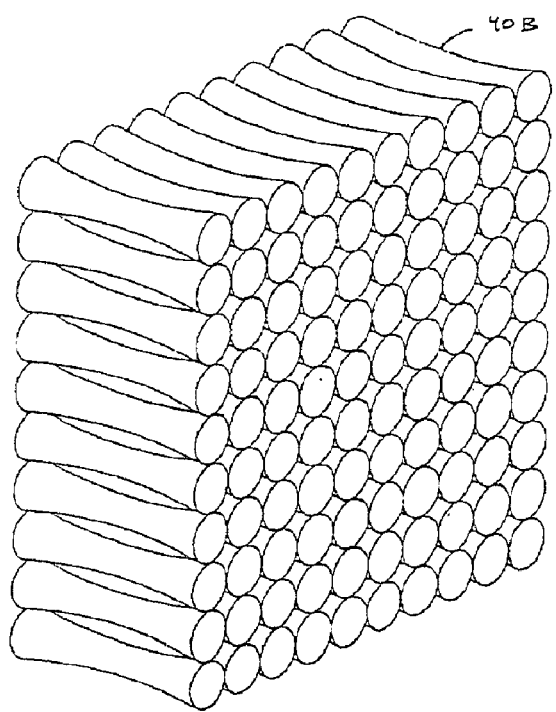
FIG. 4B is a perspective view of an alternate embodiment of the muffling means having repeating elongated cylindrical cells with varying diameters.
Figure 4E:
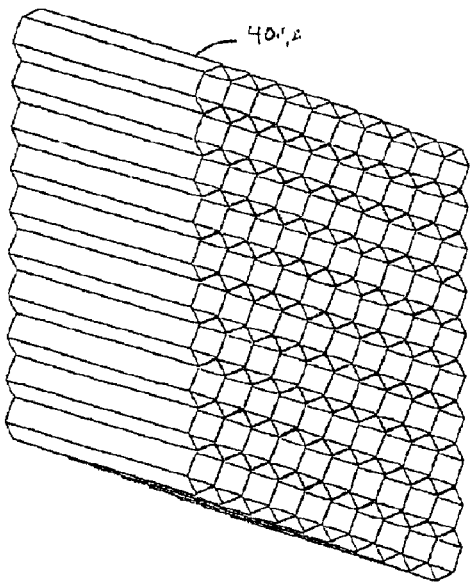
FIG. 4E is an up close perspective view of the honeycomb muffling means of FIGS. 2 and 3 having honeycomb or hexagonal cells.
Figure 4C:
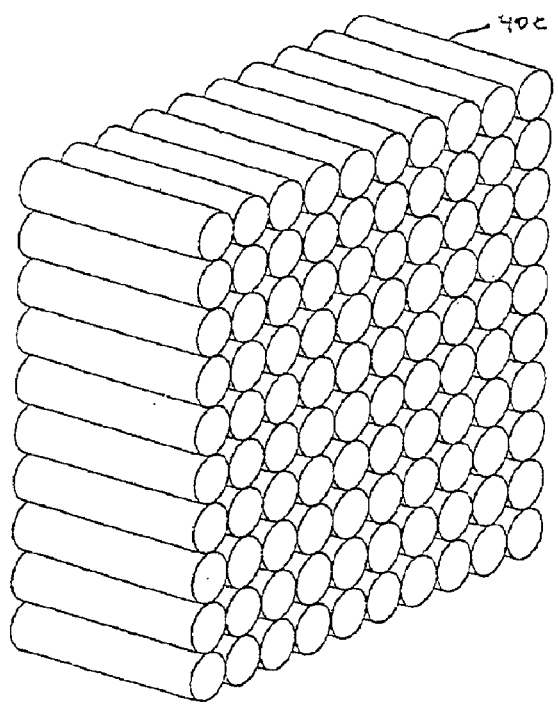
FIG. 4C is a perspective view of an alternate embodiment of the muffling means having repeating elongated cylindrical cells.
Figure 4D:
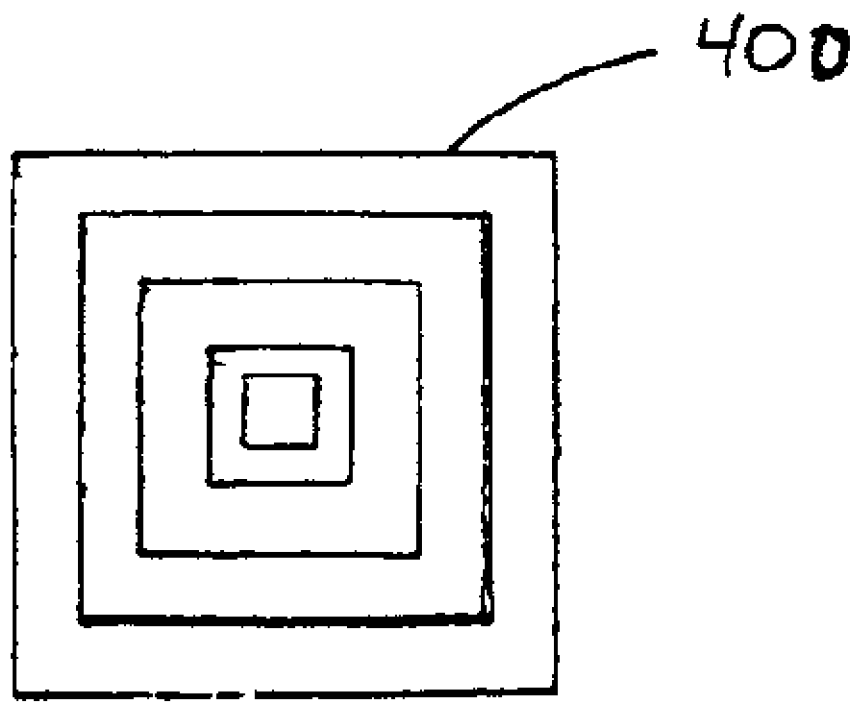
FIG. 4D is a front view of alternate embodiment of the muffling means comprising squares disposed within one another.

Although the honeycomb structure for muffling means 40 is preferred, use of any structure, disposed within negative pressure reservoir 32, having walls in-line with the initial direction of the jet flow into negative pressure reservoir 32 is anticipated. Muffling means 40 may comprise repeating cells structures with various arrangements of cells having various shapes and sizes. For example, the circular cells may be arranged in a ring or square with the center empty. FIGS. 4A–4C illustrate alternate embodiments of muffing means 40. FIG. 4A illustrates a muffling means 40A having square cells. FIG. 4B illustrates a muffling means 40B having cylindrical cells with diameters that are tapered toward the center. FIG. 4C illustrates a muffling means 40C with cylindrical cells. FIG. 4D illustrates a muffling means 40D comprising multiple squares disposed within one another. This type of arrangement of shape-within-a-shape is anticipated for other geometries as well, including hexagons and circles. FIG. 4E illustrates the hexagonal cells of honeycomb structure 40 up close.

Note also the present invention is not limited to intra-aortic balloon pump systems. The muffling means may be used in negative pressure reservoirs in any type of mechanical system requiring noise reduction.

As many apparently widely different embodiments of the present invention can be made without departing from the spirit and scope thereof, it is to be understood that the invention is not limited to the specific embodiments thereof except as defined in the appended claims.

What is claimed is:

1. A medical device pump comprising a compressor for creating a gas flow and a negative pressure reservoir connected to said compressor, said negative pressure reservoir containing a muffling means having one or more walls in-line with the initial direction of gas flow into the negative pressure reservoir.

2. The medical device pump as claimed in claim 1 further comprising a positive pressure reservoir connected to the compressor.

3. The medical device pump as claimed in claim 1 further comprising a positive pressure reservoir connected to the compressor and an isolator enclosure connected to both the positive pressure reservoir and the negative pressure reservoir, said isolator enclosure comprising an enclosed volume divided by a pliant membrane into a primary side and a secondary side.

4. The medical device pump as claimed in claim 1 further comprising a positive pressure reservoir connected to the compressor and an isolator enclosure connected to both the positive pressure reservoir and the negative pressure reservoir, said isolator enclosure comprising an enclosed volume divided by a pliant membrane into a primary side and a secondary side, said secondary side being in communication with a balloon catheter, said balloon catheter comprising a tube terminating in a balloon, shifting of the pliant membrane from side to side causes the balloon to inflate and deflate.

5. The medical device pump as claimed in claim 1 further comprising a positive pressure reservoir connected to the compressor and an isolator enclosure connected to both the positive pressure reservoir and the negative pressure reservoir, said isolator enclosure comprising an enclosed volume divided by a pliant membrane into a primary side and a secondary side, a first valve is connected between positive pressure reservoir and the primary side of the isolator, a second valve is connected between the negative pressure reservoir and the primary side of the isolator, said secondary side being in communication with a balloon catheter, said balloon catheter comprising a tube terminating in a balloon, shifting of the pliant membrane from side to side causes the balloon to inflate and deflate.

6. The medical device as claimed in claim 5 wherein the compressor maintains a predetermined vacuum level in the negative pressure reservoir and upon opening the second valve gas rushes from the primary side of the isolator into the negative pressure reservoir, the muffling means comprises one or more walls extending in-line with the initial direction of the flow into the negative pressure reservoir.

7. The medical device as claimed in claim 1 or 2 or 3 or 4 or 5 wherein decreased pressure in negative pressure reservoir created by the compressor results in a rush of gas flow into said negative pressure reservoir and wherein the muffling means is a honeycombed structure and comprises one or more walls extending in-line with the initial direction of the gas flow into the negative pressure reservoir.

8. The medical device as claimed in claim 1 or 2 or 3 or 4 or 5 wherein decreased pressure in negative pressure reservoir created by compressor results in a rush of gas flow into said negative pressure reservoir and wherein the muffling means comprises one or more walls extending in-line with the initial direction of the gas flow into the negative pressure reservoir, a transverse cross section of said one or more walls comprises one or more enclosed shapes.

9. The medical device as claimed in claim 1 or 2 or 3 or 4 or 5 wherein decreased pressure in negative pressure reservoir created by compressor results in a rush of gas flow into said negative pressure reservoir and wherein the muffling means comprises one or more walls extending in-line with the initial direction of the gas flow into the negative pressure reservoir, a transverse cross section of said one or more walls comprises one or more circles.

10. The medical device as claimed in claim 1 or 2 or 3 or 4 or 5 wherein the muffling means comprises a honeycomb structure.

11. The medical device as claimed in claim 1 or 2 or 3 or 4 or 5 wherein the muffling means comprises one or more tubes.

12. The medical device as claimed in claim 1 or 2 or 3 or 4 or 5 wherein the muffling means comprises one or more tubes disposed within one another.

13. A medical device pump comprising a compressor, a negative pressure reservoir and a positive pressure reservoir both connected to said compressor, a muffling means contained within the negative pressure reservoir, an isolator enclosure connected to both the positive pressure reservoir and the negative pressure reservoir, a first valve, and a second valve, said isolator enclosure comprising an enclosed volume divided by a pliant membrane into a primary side and a secondary side, said first valve being connected between the positive pressure reservoir and the primary side of the isolator enclosure, a second valve is connected between the negative pressure reservoir and the primary side of the isolator enclosure, said secondary side being in communication with a balloon catheter, said balloon catheter comprising a tube terminating in a balloon, shifting of the pliant membrane from side to side causes the balloon to inflate and deflate, said compressor maintains a predetermined vacuum level in the negative pressure reservoir and upon opening the second valve gas rushes from the primary side of the isolator into the negative pressure reservoir, the muffling means comprises one or more walls extending in-line with the initial direction of the gas flow into the negative pressure reservoir as is of a honeycombed structure.

14. The medical device pump as claimed in claim 13 wherein the muffling means comprises a honeycomb structure disposed within the negative pressure reservoir.

\* \* \* \* \*